(12) United States Patent
Van Nguyen et al.

(10) Patent No.: US 8,637,489 B2
(45) Date of Patent: Jan. 28, 2014

(54) CLEAR CARRIER COMPOSITIONS FOR LIPOPHILIC COMPOUNDS, AND METHOD OF TREATING KERATINOUS SUBSTRATES USING SUCH COMPOSITIONS

(75) Inventors: Nghi Van Nguyen, Edison, NJ (US); Sawa Hashimoto, Westfield, NJ (US); David W. Cannell, New Hope, PA (US)

(73) Assignee: L'Oreal, Paris (FR)

( * ) Notice: Subject to any disclaimer, the term of this patent is extended or adjusted under 35 U.S.C. 154(b) by 531 days.

(21) Appl. No.: 12/701,227

(22) Filed: Feb. 5, 2010

(65) Prior Publication Data

US 2010/0202999 A1 Aug. 12, 2010

Related U.S. Application Data

(60) Provisional application No. 61/150,814, filed on Feb. 9, 2009, provisional application No. 61/150,816, filed on Feb. 9, 2009, provisional application No. 61/150,818, filed on Feb. 9, 2009, provisional application No. 61/150,820, filed on Feb. 9, 2009, provisional application No. 61/150,822, filed on Feb. 9, 2009, provisional application No. 61/150,823, filed on Feb. 9, 2009, provisional application No. 61/150,825, filed on Feb. 9, 2009, provisional application No. 61/150,829, filed on Feb. 9, 2009.

(51) Int. Cl.
*A61K 31/695* (2006.01)
*A61K 9/10* (2006.01)

(52) U.S. Cl.
USPC .......................... 514/63; 424/401; 424/70.1

(58) Field of Classification Search
USPC .................... 514/63; 424/401, 70.1
See application file for complete search history.

(56) References Cited

U.S. PATENT DOCUMENTS

| | | | |
|---|---|---|---|
| 4,488,564 A | 12/1984 | Grollier | |
| 5,070,171 A | 12/1991 | O'Lenick | |
| 5,093,452 A | 3/1992 | O'Lenick | |
| 5,149,765 A | 9/1992 | O'Lenick | |
| 5,223,244 A | 6/1993 | Moro | |
| 5,248,783 A | 9/1993 | O'Lenick | |
| 5,739,371 A | 4/1998 | O'Lenick | |
| 5,747,435 A | 5/1998 | Patel | |
| 5,853,705 A | 12/1998 | Nakayama | |
| 5,866,144 A | 2/1999 | Chopra | |
| 6,191,083 B1 | 2/2001 | Brooks | |
| 6,218,345 B1 | 4/2001 | Brooks | |
| 6,419,962 B1 | 7/2002 | Yokoyama | |
| 6,426,063 B1 | 7/2002 | Schuler | |
| 6,946,124 B2 | 9/2005 | Arnaud-Sebillotte | |
| 7,147,873 B2 | 12/2006 | Scholz | |
| 7,157,413 B2 | 1/2007 | Lazzeri | |
| 7,323,163 B2 | 1/2008 | Wang | |
| 2002/0006389 A1 | 1/2002 | Restle | |
| 2002/0010215 A1 | 1/2002 | Shiroyama | |
| 2002/0034489 A1 | 3/2002 | Wiegland | |
| 2002/0193265 A1 | 12/2002 | Perron | |
| 2003/0091602 A1 | 5/2003 | Witteler et al. | |
| 2004/0033984 A1 | 2/2004 | Muller | |
| 2004/0185020 A1 | 9/2004 | Gawtrey | |
| 2004/0266886 A1 | 12/2004 | Seipel | |
| 2005/0031566 A1 | 2/2005 | Cooper | |
| 2005/0032668 A1 | 2/2005 | Pedersen et al. | |
| 2005/0084471 A1 | 4/2005 | Andrews | |
| 2005/0089539 A1 | 4/2005 | Scholz | |
| 2006/0051384 A1 | 3/2006 | Scholz | |
| 2006/0051385 A1 | 3/2006 | Scholz | |
| 2006/0052452 A1 | 3/2006 | Scholz | |
| 2006/0159782 A1 | 7/2006 | Amano | |
| 2006/0286057 A1* | 12/2006 | Cannell et al. | 424/70.12 |
| 2007/0041927 A1 | 2/2007 | Blaeser et al. | |
| 2008/0038215 A1 | 2/2008 | Derici | |
| 2008/0085258 A1* | 4/2008 | Nguyen et al. | 424/70.122 |
| 2009/0202465 A1 | 8/2009 | Mougin et al. | |
| 2010/0202988 A1 | 8/2010 | Nguyen et al. | |
| 2010/0202995 A1 | 8/2010 | Nguyen et al. | |
| 2010/0203000 A1 | 8/2010 | Nguyen et al. | |

FOREIGN PATENT DOCUMENTS

| | | |
|---|---|---|
| EP | 510879 A3 | 3/1993 |
| EP | 0532272 A3 | 3/1993 |
| EP | 1213007 A3 | 6/2002 |
| EP | 1535602 A1 | 6/2005 |
| EP | 1739161 A1 | 4/2009 |
| JP | 2003105669 A | 4/2003 |
| JP | 2006028096 A | 2/2006 |

(Continued)

OTHER PUBLICATIONS

Flick, E., "Anti-Frizz Formulas with PrimaFlo HP-22 (Formulation A)", Cosmetics and Toiletries Formulations Database, 2005, William Andrew Publishing.*
Flick, E., Cosmetics Additives, 1991, Noyes Publications, p. 674.*
Lupasol Product Range: preliminary technical information, Sep. 1996, BASF.*
Tsiourvas, D; Arkas, M.; Paleos, C. M.; Skoulios, A. "Smectic mesomorphism of long-chain n-Alkylammonium polyacrylates" Polymer Preprints (American Chemical Society, Division of Polymer Chemistry) (1997), 36(1), p. 233-234.
Amendment filed in U.S. Appl. No. 12/701,195 on Jul. 25, 2013.

(Continued)

*Primary Examiner* — Gina C Justice
(74) *Attorney, Agent, or Firm* — L''Oreal USA

(57) ABSTRACT

The present invention relates to a composition comprising:
(a) at least one alkoxylated silicone acid;
(b) at least one amino compound chosen from polyamines, alkoxylated polyamines, alkyl monoamines, alkoxylated monoamines and mixtures thereof;
(c) at least one lipophilic compound; and
(d) at least one solvent comprising water.
Such a composition is clear in appearance, and stable.
The present invention also relates to a method of making such a clear composition, and to a method of cosmetic treatment of a keratinous substrate using such a composition.

46 Claims, No Drawings

(56) References Cited

FOREIGN PATENT DOCUMENTS

| WO | WO 98/00494 A1 | 1/1998 |
| WO | WO 2006/010440 A1 | 2/2006 |
| WO | WO 2006/010441 A1 | 2/2006 |
| WO | WO 2006/045418 A1 | 5/2006 |
| WO | WO 2006/099358 A3 | 9/2006 |
| WO | WO 2007/003784 A1 | 1/2007 |

OTHER PUBLICATIONS

John A. Wenninger, G.N. McEwen, Jr., International Cosmetic Ingredient Dictionary and Handbook, 1997, 7th Edition, published by The Cosmetic, Toiletry and Fragrance Association Inc. (CTFA), 1101 17th Street, N.W., Suite 300, Washington, DC, USA.

Zhongshan Kemei Oleochemicals Co., Ltd (http://daily-chemical-raw-materials.com/products; downloaded Nov. 16, 2012).

* cited by examiner

US 8,637,489 B2

CLEAR CARRIER COMPOSITIONS FOR LIPOPHILIC COMPOUNDS, AND METHOD OF TREATING KERATINOUS SUBSTRATES USING SUCH COMPOSITIONS

REFERENCE TO PRIOR APPLICATIONS

This application claims the benefit of priority under 35 U.S.C. §119(e) from U.S. provisional application Ser. Nos. 61/150,814, 61/150,816, 61/150,818, 61/150,820, 61/150,822, 61/150,823, 61/150,825 and 61/150,829, filed Feb. 9, 2009, incorporated herein by reference in their entirety.

TECHNICAL FIELD

The present invention relates to carrier compositions comprising lipophilic ingredients. More particularly, the present invention provides for a clear composition containing one or more lipophilic ingredients, which remains clear even when diluted in particular with water.

The invention further relates to methods of treating keratinous substrates using such compositions.

BACKGROUND OF THE DISCLOSURE

Cosmetic and personal care products are available in various forms and one of the forms that are desired by many consumers is a clear aqueous product. At the same time, the consumer expects that such a product will provide desirable cosmetic benefits to keratinous substrates such as hair and skin.

These cosmetic benefits can be provided by the presence of water-insoluble ingredients, for example, oils, silicones and other lipophilic materials, in the product.

However, certain water-insoluble ingredients, which are oftentimes desirable for the treatment of keratinous substrates, are inherently difficult to incorporate into aqueous systems, such as shampoos, conditioners and skin care compositions, without forming a traditional emulsion in either cream or lotion form. Oftentimes, the presence of such ingredients at levels that would impart appreciable cosmetic benefits to hair or skin and/or properties to cosmetic and personal care products results in unstable formulations resulting in undesirable phase separations in aqueous systems.

Therefore, in the formulation of clear aqueous compositions, water-insoluble compounds do not lend themselves to being used therein, due to their inability to significantly associate with the water present in the system. As a result, the presence of these water-insoluble ingredients is generally minimal in personal care products and cosmetic products that employ aqueous systems. Thus, the difficulties in formulating such compositions deprives the consumer of products that can better deliver cosmetic benefits to hair and skin such as conditioning, cleansing, coloring of hair, styling of hair, skin care, and better application and spreadability of products.

Thus, there remains a need for an aqueous composition which can carry increased amounts of water-insoluble materials while remaining both homogeneous and clear in appearance. There also remains a need for an aqueous system which can carry increased amounts of water-insoluble materials such as oils and other lipophilic ingredients in order to deliver desirable benefits to hair and skin.

It has been surprisingly and unexpectedly discovered that the combination of at least one alkoxylated silicone acid, at least one amino compound chosen from polyamines, alkoxylated polyamines, alkyl monoamines, alkoxylated monoamines and mixtures thereof, at least one solvent, and at least one water-insoluble compound such as a lipophilic compound, yields a composition which is clear in appearance and stable. Moreover, the inventive composition remains clear and stable even if additional solvent such as in particular water is added thereto.

It has also been discovered that the use of this clear composition on keratinous substrates, such as hair and skin, results in desirable and beneficial effects on the substrates, such as in particular improved delivery of active ingredients, improved cosmetic effects such as improved color retention on colored-treated hair, improved conditioning, improved hair styling effects and manageability, improved shine, improved protection from environmental and chemical damage, and enhanced color is the case of coloring compositions.

BRIEF SUMMARY OF THE DISCLOSURE

The present invention is directed to a composition comprising:
  (a) at least one alkoxylated silicone acid;
  (b) at least one amino compound chosen from polyamines, alkoxylated polyamines, alkyl monoamines, alkoxylated monoamines and mixtures thereof;
  (c) at least one lipophilic compound; and
  (d) at least one solvent comprising water.
Such a composition is clear in appearance, and stable.

The present invention is also directed to a method of making a clear composition involving the steps of:
  (a) providing at least one alkoxylated silicone acid;
  (b) providing at least one amino compound chosen from polyamines, alkoxylated polyamines, alkyl monoamines, alkoxylated monoamines and mixtures thereof;
  (c) providing at least one lipophilic compound;
  (d) providing at least one solvent comprising water; and
  (e) mixing the compounds as defined in steps (a) to (d) to form a composition that is clear in appearance.

The present invention is further directed to a method of cosmetic treatment of a keratinous substrate involving the step of applying onto said keratinous substrate a composition as defined herein.

DETAILED DESCRIPTION OF THE DISCLOSURE

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

Other than in the operating examples, or where otherwise indicated, all numbers expressing quantities of ingredients and/or reaction conditions are to be understood as being modified in all instances by the term "about".

The term "lipophilic" means those compounds which are soluble in oils and either completely or partially insoluble in water. In accordance with the present invention, the lipophilic compounds preferably have a solubility in water at 25° C. and at atmospheric pressure of less than 5% by weight, more preferably less than 1% by weight, even more preferably less than 0.5% by weight and better still less than 0.1% by weight.

"At least one" as used herein means one or more and thus includes individual components as well as mixtures/combinations thereof.

The term "clear" as used herein means transparent such that a person is able to see through the composition with their naked eye. The term "clear" as used herein is not meant to encompass those compositions which a person cannot see through with their naked eye such as those which are pearlescent, frosted, hazy, opaque, or cloudy in appearance.

The clarity of the compositions of the present invention can be determined using the McFarland scale, which is based on the McFarland Equivalence Turbidity Standard Test (Remel, 12076 Santa Fe Drive, Lenexa, Kans. 66215, USA). Preferably, the compositions according to the present invention have a McFarland turbidity standard value, as visually determined, equal to or less than 0.5 on the McFarland scale.

The term "stable" as used herein means that the composition does not exhibit phase separation.

The term "carrier system for lipophilic compounds" means a system that delivers a lipophilic ingredient into an aqueous phase by incorporation or solubilization. The lipophilic carrier system of the present invention is capable of bringing lipophilic compounds into an aqueous phase such that the aqueous phase remains clear and stable.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Alkoxylated" as used herein means comprising at least one alkoxy group. As used herein, an alkoxy group is a group corresponding to the formula —O—CHR—$(CH_2)_n$—, wherein R represents H or a C1-C5 alkyl group, and wherein n is an integer ranging from 1 to 6.

Alkoxylated Silicone Acids

The alkoxylated silicone acids of the present invention are silicone compounds comprising at least one acid group and one or more alkoxy groups as defined above.

Preferably, the alkoxylated silicone acid of the present invention is a polyacid, that is to say a compound comprising at least two acid groups.

The alkoxy group(s) may be chosen from terminal alkoxy groups, pendant alkoxy groups, and alkoxy groups which are intercalated in the skeleton of the silicone compound. The alkoxy groups are preferably chosen from ethylene oxide groups ("EO"=—$CH_2$—$CH_2$—O—), propylene oxide groups ("PO"=—$C_3H_6O$—) and mixtures thereof.

Preferably, the at least one alkoxylated silicone acid of the present invention is chosen from alkoxylated silicone carboxylates, alkoxylated silicone phosphates, alkoxylated silicone sulfates, alkoxylated silicone sulfosuccinates, and alkoxylated silicone sulfonates. These compounds are also known as alkoxylated anionic silicones.

Suitable alkoxylated silicone carboxylates for use in the compositions of the present invention are chosen from silicone compounds comprising at least one carboxylic acid group and at least one alkoxylated chain. Such silicone carboxylates may be chosen from those which are water soluble, oil soluble, water-dispersible and/or soluble in organic solvents.

The at least one carboxylic acid group in the silicone carboxylates of the present invention may be chosen from terminal carboxylic acid groups and pendant carboxylic acid groups.

In one embodiment, the alkoxylated silicone carboxylates of the present invention are chosen from silicone compounds of formula (I) and salts thereof:

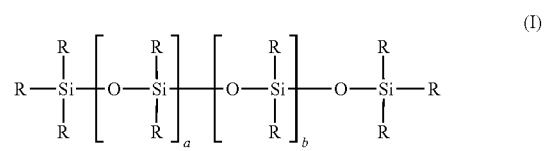

wherein: a is an integer ranging from 0 to 100; b is an integer ranging from 0 to 500; R, which may be identical or different, are each chosen from optionally substituted hydrocarbon groups comprising from 1 to 9 carbon atoms, optionally substituted phenyl groups, and groups of formula (II):

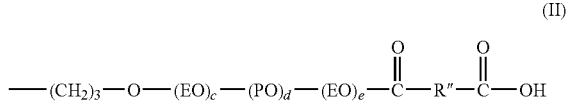

wherein: c, d, and e, which may be identical or different, are each integers ranging from 0 to 20; EO is an ethylene oxide group; PO is a propylene oxide group; and R" is chosen from optionally substituted divalent hydrocarbons, such as alkylene groups and alkenylene groups comprising from 2 to 22 carbon atoms, and optionally substituted divalent aromatic groups, such as groups of formula (III):

and groups of formula (IV):

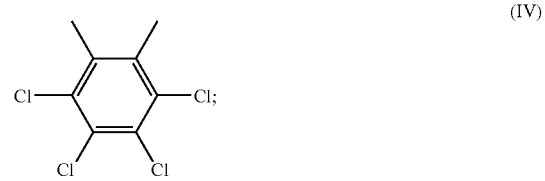

with the proviso that at least one of the R groups is chosen from groups of formula (II).

Non-limiting examples of alkoxylated silicone carboxylates include those commercially available from the company Lubrizol under the name Ultrasil CA-1 Silicone and Ultrasil® CA-2 Silicone, both of which correspond to formula (V) below. These silicone carboxylates are sold in the free acid form as an emulsifier and dispersing aid for complexing fatty cationic amines and quaternary amines.

Thus, in one particularly preferred embodiment, the at least one alkoxylated silicone acid is chosen from silicone compounds of formula (V) and salts thereof:

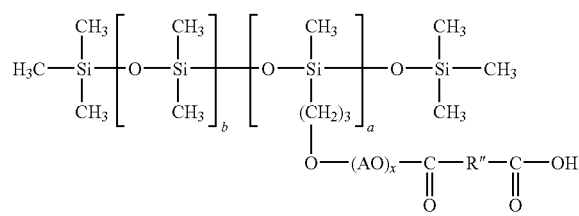

(V)

wherein: a is an integer ranging from 2 to 100; b is an integer ranging from 0 to 500; AO is chosen from groups of formula (VI):

(VI)

wherein: c, d, and e, which may be identical or different, are each integers ranging from 0 to 20 with the proviso that the sum c+d+e is at least 1; EO is an ethylene oxide group; and PO is a propylene oxide group; x is an integer ranging from 1 to 60; R'' is chosen from optionally substituted divalent hydrocarbons, such as alkylene groups and alkenylene groups comprising from 2 to 22 carbon atoms, and optionally substituted divalent aromatic groups, such as groups of formula (III):

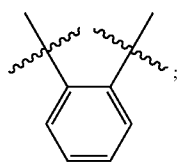

(III)

and groups of formula (IV):

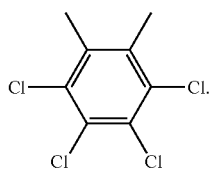

(IV)

Non-limiting examples of alkoxylated silicone carboxylates useful in the present invention include those described in U.S. Pat. Nos. 5,248,783 and 5,739,371, the disclosures of which are incorporated herein by reference, and which are silicone compounds of formula (I).

Suitable alkoxylated silicone phosphates for use in the compositions of the present invention are chosen from silicone compounds comprising at least one phosphate group and at least one alkoxylated chain. Such silicone phosphates may be chosen from those which are water soluble, oil soluble, water-dispersible and/or soluble in organic solvents.

The at least one phosphate group in the alkoxylated silicone phosphates of the present invention may be chosen from terminal phosphate groups and pendant phosphate groups.

Further, the at least one phosphate group may be chosen from groups of formula —O—P(O)(OH)$_2$, groups of formula —O—P(O)(OH)(OR), and groups of formula —O—P(O)(OR)$_2$, wherein R may be chosen from H, inorganic cations, and organic cations. Non-limiting examples of inorganic cations include alkali metals, such as, for example, potassium lithium, and sodium. A non-limiting example of organic cation is at least one additional silicone compound which may be identical to or different from the at least one silicone compound bonded to the other oxygen of the phosphate group.

In one preferred embodiment, the at least one alkoxylated silicone phosphate is chosen from silicone compounds of formula (VII) and salts thereof:

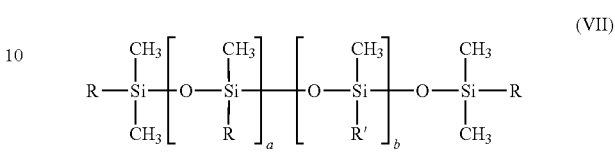

(VII)

wherein:
a is an integer ranging from 0 to 200;
b is an integer ranging from 2 to 500;
R is chosen from —OH, and alkyl groups containing 1 to 9 carbon atoms;
R' is represented by formula (VIII):

(VIII)

wherein
R'' is chosen from alkylene groups containing 1 to 10 carbon atoms;
c, d, and e, which may be identical or different, are each integers ranging from 0 to 20 with the proviso that the sum c+d+e is at least 1;
R''' is a phosphate group chosen from groups of formula —O—P(O)(OH)$_2$, groups of formula —O—P(O)(OH)(OR1), and groups of formula —O—P(O)(OR1)$_2$, wherein R1 is chosen from hydrogen, inorganic cations, and organic cations.

In one particularly preferred embodiment, the at least one alkoxylated silicone acid is chosen from Dimethicone PEG-8 phosphate, Dimethicone PEG-7 phosphate and mixtures thereof.

Non-limiting examples of suitable alkoxylated silicone phosphates include those commercially available from the company Phoenix Chemical, Inc. of New Jersey under the name of Pecosil®, such as Pecosil® PS-100, Pecosil® PS-112, Pecosil® PS-150, Pecosil® PS-200, Pecosil® WDS-100, Pecosil® WDS-200, Pecosil® PS-100 B, and Pecosil® PS-100 K and those commercially available from the company Siltech under the name Silphos A-100 and Silphos A-150. Other non-limiting examples of suitable alkoxylated silicone phosphates include those described in U.S. Pat. Nos. 5,070,171, 5,093,452, and 5,149,765 the disclosures of which are incorporated herein by reference.

Suitable alkoxylated silicone sulfates for use in the present invention include silicone compounds comprising at least one sulfate group and at least one alkoxylated chain represented by formula (IX):

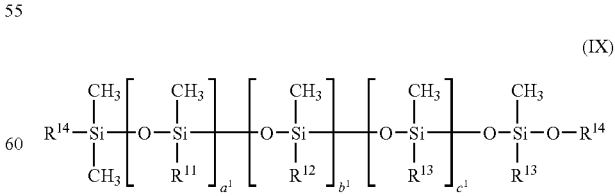

(IX)

wherein $R^{11}$ is selected from lower alkyl having one to eight carbon atoms or phenyl, $R^{12}$ is —(CH$_2$)$_3$—O-(EO)$_x$—(PO)$_y$-(EO)$_z$—SO$_3$-M wherein M is a cation and is selected from Na, K, Li, or NH$_4$ and wherein EO is an ethylene oxide group and PO is a propylene oxide group and x, y and z are integers independently ranging from 0 to 100 with the proviso that the sum x+y+z is at least 1; $R^{13}$ is —$(CH_2)_3$—O-$(EO)_x$—$(PO)_y$-$(EO)_z$—H with x, y and z being integers independently ranging from 0 to 100 with the proviso that the sum x+y+z is at least 1; $R^{14}$ is methyl or hydroxyl; $a^1$ and $c^1$ are independently integers ranging from 0 to 50; $b^1$ is an integer ranging from 2 to 50. An example of corresponding available commercial product is the Ultrasil SA-1 silicone sold by the company Lubrizol.

Suitable alkoxylated silicone sulfosuccinates of use in the present invention are silicone compounds comprising at least one phosphate group and at least one alkoxylated chain and include, but are not limited to, those corresponding to formula (X):

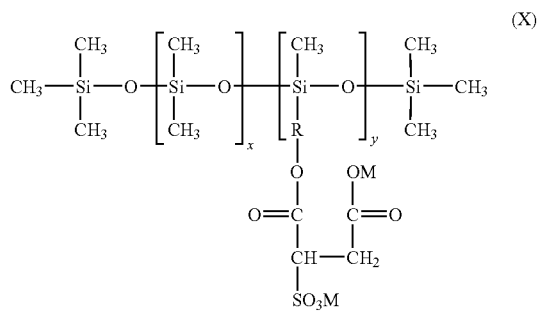

wherein R represents a divalent radical selected from

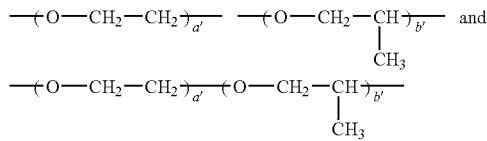

wherein a' and b' are integers ranging independently from 0 to 30 with the proviso that the sum a'+b' is at least 1; x is an integer ranging from 0 to 200; y is an integer ranging from 2 to 200; and M is an alkali metal such as sodium or potassium, or an ammonium group.

Particularly preferred alkoxyalted silicone acids are Dimethicone PEG-8 phosphate (known under the tradename Silsense PE-100L Silicone—formerly Ultrasil PE-100, and commercially available from the company Lubrizol, Dimethicone PEG-7 phosphate (known under the tradenames Pecosil PS-100, and Pecosil PS-112, commercially available from Phoenix Chemical Inc) and mixtures thereof.

The at least one alkoxylated silicone acid is preferably present in the composition in an amount of from 1 to 50% by weight, more preferably from 2 to 40% by weight, and even more preferably from 5 to 30% by weight, based on the total weight of the composition.

Alkoxylated Polyamines

Non-limiting preferred examples of suitable alkoxylated polyamines include hydrocarbyl amines which have at least one primary nitrogen atom and include compounds corresponding to formula (IA):

$$NH_2R(R'CHCH_2O)_x(R'CHCH_2O)_y(R'CHCH_2O)_z$$
$$RNH_2 \quad (IA)$$

wherein R represents a —$CHCH_3$— or —$C(CH_3)_2$— group, or a hydrocarbon radical containing at least 3 carbon atoms that is linear or branched, acyclic or cyclic, saturated or unsaturated, aliphatic or aromatic, substituted or unsubstituted;

x, y, and z independently of one another, represent numbers of from 0 to 100;

R' represents hydrogen, or an alkyl group, preferably a methyl group; and the sum of x+y+z is at least 1.

In formula (IA), R is preferably a linear or branched, acyclic alkyl or alkenyl group or an alkyl phenyl group; x, y, and z independently of one another, preferably represent numbers ranging from 2 to 100.

Examples of the alkoxylated polyamines for use in the present invention which correspond to formula (IA) include, for example, tetradecyloxypropyl-1,3-diaminopropane; a $C_{12-14}$ alkyl oxypropyl-1,3-diaminopropane; a $C_{12-15}$ alkyloxypropyl amine and other similar materials that are commercially available from Tomah under the tradename of TOMAH® DA-17.

Other examples of alkoxylated polyamines of Formula (IA) are diamine compounds belonging to the Jeffamine series such as the Jeffamine® D and Jeffamine® ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. Jeffamine® D series compounds are amine terminated PPGs (polypropylene glycols) and Jeffamine® ED series compounds are polyether diamine based with a predominantly PEG (polyethylene glycol) backbone.

Other non-limiting preferred examples of suitable alkoxylated polyamines in the diamine form include compounds corresponding to formula (IIA):

$$NH_2(CH_2)_xOCH_2CH_2O(CH_2)_xH_2 \quad (IIA)$$

wherein x is 2 or 3.

Examples of alkoxylated polyamines of Formula (IIA) are diamine compounds belonging to the JEFFAMINE series available from Huntsman Corporation, Salt Lake City, Utah, such as JEFFAMINE EDR148, and JEFFAMINE EDR176.

Additional non-limiting preferred examples of alkoxylated polyamines in the triamine form include compounds corresponding to formula (IIIA):

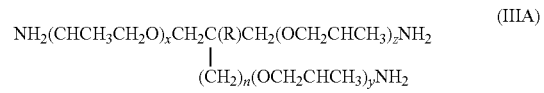

wherein R is hydrogen or —$C_2H_5$,
n=0 or 1, and
x, y, and z independently of one another, represent numbers of from 0 to 100 and the sum of x+y+z is at least 1.

Examples of alkoxylated polyamines for use in the present invention which correspond to formula (IIIA) are triamine compounds belonging to the Jeffamine series such as the Jeffamine® T series available from Huntsman Corporation, Salt Lake City, Utah. Examples of the Jeffamine® T series compounds are JEFFAMINE T403, JEFFAMINE T3000, and JEFFAMINE T5000. Jeffamine® T series compounds are triamines made by reacting PO with a triol initiator followed by aminating the terminal hydroxyl groups.

Another type of preferred alkoxylated polyamines include compounds of formulas (IVA) and (VA) hereunder:

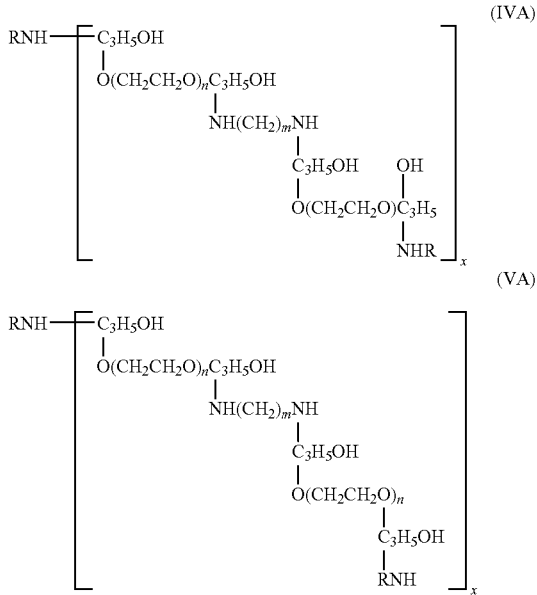

(IVA)

(VA)

wherein
R in formula (IVA) represents the alkyl group derived from tallow and R in formula (VA) represents the alkyl group derived from coconut oil;
n in both formulas (IVA) and (VA) has a total value ranging from 10 to 20;
m in both formulas (IVA) and (VA) has a value ranging from 2 to 6; and
x in both formulas (IVA) and (VA) has a value ranging from 2 to 4.

Examples of alkoxylated polyamines of Formulas (IVA) and (VA) are PEG-15 Tallow Polyamine and PEG-15 Cocopolyamine, respectively.

The at least one alkoxylated polyamine can be present in the composition of the present invention a preferred amount ranging from 0.1 to 50% by weight, preferably from 0.5 to 15% by weight, more preferably from 0.5 to 10% by weight, based on the total weight of the composition.

Alkyl Monoamines

Non-limiting examples of preferred alkyl monoamines include aliphatic amine compounds corresponding to formula (IB) and their salts:

wherein
R is a hydrocarbon radical containing at least 6 carbon atoms, preferably from 8 to 30 carbon atoms, more preferably from 12 to 24 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and
R' is H or a hydrocarbon radical containing less than 6 carbon atoms. In addition, R' is linear or branched, acyclic or cyclic, saturated or unsaturated, substituted or unsubstituted. Typically, R' is a linear or branched, acyclic alkyl or alkenyl group. Preferably, R' is H or a methyl group.

Preferred alkyl monoamines include, but are not limited to the following examples: dimethyl lauramine, dimethyl behenamine, dimethyl cocamine, dimethyl myristamine, dimethyl palmitamine, dimethyl stearamine, dimethyl tallowamine, dimethyl soyamine, stearamine, soyamine, cocamine, lauramine, palmitamine, oleamine, tallow amine and mixtures thereof.

Other non-limiting examples of preferred alkyl monoamines include amidoamine compounds corresponding to formula (IIB) and their salts:

wherein:
R is a hydrocarbon radical containing at least 6 carbon atoms, preferably from 8 to 30 carbon atoms, more preferably from 12 to 24 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and
R' is a divalent hydrocarbon radical containing less than 6 carbon atoms, preferably 2 or 3 carbon atoms, and
R" is H or a hydrocarbon radical containing less than 6 carbon atoms. In addition, R" is linear or branched, acyclic or cyclic, saturated or unsaturated, substituted or unsubstituted. Typically, R" is a linear or branched, acyclic alkyl or alkenyl group. Preferably, R" is H or a methyl group.

Preferred amidoamines include, but are not limited to the following examples: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and mixtures thereof.

The at least one alkyl monoamine can be present in the composition of the present invention in an amount of from 0.1 to 50% by weight, preferably from 0.5 to 30% by weight, and more preferably from 1 to 20% by weight, based on the total weight of the composition.

Polyamines

The polyamines may in particular be chosen from polyethyleneimines, polyvinylamines, aminated polysaccharides, amine substituted polyalkylene glycols, amine substituted polyacrylate crosspolymers, amine substituted polyacrylates, amine substituted polymethacrylates, proteins, protein derivatives, amine substituted polyesters, polyamino acids, polyalkylamines, diethylene triamine, triethylenetetramine, spermidine, spermine and mixtures thereof.

Preferred polyethyleneimine include those of formula (IC):

wherein n is an integer ranging from 5 to 5000, preferably from 10 to 2500.

Such polyethyleneimine are commercially available from BASF under the trade name Lupasol®. Suitable examples of Lupasol® polyethyleneimines include Lupasol® PS, Lupasol® PL, Lupasol® PR8515, Lupasol® G20, Lupasol® G35 as well as Lupasol® SC Polyethyleneimine Reaction Products (such as Lupasol® SC-61B, Lupasol® SC-62J, and Lupasol® SC-86x). Other non-limiting examples of polyethyleneimines which may be used in the composition according to the present invention are the Epomin® products commercially available from Aceto. Suitable examples of Epomin® polyethyleneimines include Epomin® SP-006, Epomin® SP-012, Epomin® SP-018, and Epomin® P-1000. These examples include substituted polyethyleneimines.

Non-limiting examples of polyvinylamines include the products sold under the trade name Lupamines® 9095, 9030, 9010, 5095 and 1595 from BASF.

An example of an amine substituted polyalkylene glycol includes PEG-15 cocopolyamine, available from Cognis.

An example of an amine substituted polyacrylate crosspolymer includes the product sold under the name Carbopol® Aqua CC polymer by Lubrizol Advanced Materials, Inc.

In another embodiment, the polyamine compound is chosen from proteins and protein derivatives. In one preferred embodiment, the at least one polyamine compound is chosen from wheat protein, soy protein, oat protein, collagen, and keratin protein.

In another preferred embodiment, the polyamine compound is chosen from compounds comprising lysine, compounds comprising arginine, compounds comprising histidine, and compounds comprising hydroxylysine. Non limiting examples include chitosan, and polyamino acids such as polyarginine and polylysine.

In another preferred embodiment, the polyamine compound is chosen from PEG-15 Tallow Polyamine, PEG-15 Cocopolyamine, and mixtures, thereof.

According to a particularly preferred embodiment, the polyamine is chosen from polyethyleneimines of formula (IC) as described above.

The at least one polyamine can be present in the composition of the present invention in an amount of from 0.1 to 50% by weight, preferably from 0.25 to 30% by weight, and more preferably from 0.5 to 15% by weight, based on the total weight of the composition.

Alkoxylated Monoamines

Non-limiting preferred examples of suitable alkoxylated monoamines include compounds corresponding to the formula (ID):

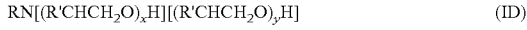

$$RN[(R'CHCH_2O)_xH][(R'CHCH_2O)_yH] \qquad (ID)$$

wherein R is a hydrocarbon radical containing at least 6 carbon atoms, preferably from 8 to 30 carbon atoms, more preferably from 12 to 24 carbon atoms. R can be linear or branched, acyclic or cyclic, saturated or unsaturated, aliphatic or aromatic, substituted or unsubstituted.

x and y, independently of one another, represent numbers of from 0 to 100 provided that the sum of x+y is >0;

the groups R', which may be identical or different, represent hydrogen, or an alkyl group such as in particular a methyl group.

Typically, R is a linear or branched, acyclic alkyl or alkenyl group or an alkyl phenyl group; x and y, independently of one another, are each typically a number from 0 to 30. Typically, one R' group is hydrogen, and the other one is methyl.

Examples of preferred alkoxylated monoamines for use in the present invention which correspond to formula (ID) are PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseedamine, PEG-2 Oleamine, PEG-5 Oleamine, PEG-6 Oleamine, PEG-10 Oleamine, PEG-15 Oleamine, PEG-20 Oleamine, PEG-25 Oleamine, and PEG-30 Oleamine. Other examples are alkoxylated derivatives of soyamine, stearamine and tallow amine.

Other non-limiting examples of suitable alkoxylated monoamines include compounds corresponding to formula (IID):

$$RNR''[(R'CHCH_2O)_xH] \qquad (IID)$$

wherein R is a hydrocarbon radical, containing at least 6 carbon atoms, preferably from 8 to 30 carbon atoms, more preferably from 12 to 24 carbon atoms. R can be linear or branched, acyclic or cyclic, saturated or unsaturated, aliphatic or aromatic, substituted or unsubstituted.

x represents a number of from 1 to 100;

R' represents hydrogen, or an alkyl group such as in particular a methyl group; and R" is a hydrogen or a hydrocarbon radical.

Typically, R is a linear or branched, acyclic alkyl or alkenyl group or an alkyl phenyl group; x is typically a number from 1 to 30.

When R" in formula (IID) is a hydrocarbon radical group, this group may be linear or branched, saturated or unsaturated, substituted or unsubstituted. The hydrocarbon radical represented by R" may also contain an alkoxylated moiety (as defined by $[(R'CHCH_2O)_yH]$), and/or heteroatoms such as nitrogen. When R" contains at least one alkoxylated moiety, the total number of alkoxylation in the formula may range from 1 to 120.

Examples of alkoxylated monoamines for use in the present invention which correspond to formula (IID) are PEG-3 Tallow Aminopropylamine, PEG-10 Tallow Aminopropylamine, PEG-Tallow Aminopropylamine, and PEG-105 Behenyl Propylenediamine.

Additional non-limiting examples of alkoxylated monoamines include compounds corresponding to formula (IIID):

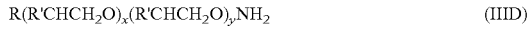

$$R(R'CHCH_2O)_x(R'CHCH_2O)_yNH_2 \qquad (IIID)$$

wherein R is a hydrocarbon radical containing at least 6 carbon atoms, preferably from 8 to 30 carbon atoms, more preferably from 12 to 24 carbon atoms. R can be linear or branched, acyclic or cyclic, saturated or unsaturated, aliphatic or aromatic, substituted or unsubstituted.

x and y, independently of one another, represent numbers of from 0 to 100 with the proviso that the sum of x+y is >0;

the groups R', which may be identical or different, represent hydrogen, or an alkyl group such as in particular a methyl group.

Typically, R is a linear or branched, acyclic alkyl or alkenyl group or an alkyl phenyl group; x and y, independently of one another, are each typically a number from 0 to 30.

Examples of alkoxylated monoamines for use in the present invention which correspond to formula (IIID) are polyetheramines containing a monoamine group. These polyetheramines are commercially available from Hunstman under the tradename Jeffamine (M series such as M-600, M-1000, M-2005 and M-2070) and Surfonamine series (B-60, B-100, B-200, L-100, L-200, L-207, L-300).

The at least one alkoxylated monoamine can be present in the composition in an amount of from 0.1 to 50% by weight, preferably from 0.5 to 30% by weight, more preferably from 1 to 20% by weight, based on the total weight of the composition.

Preferably, the ratio of the acid number of the at least one alkoxylated silicone acid to the total amine number of amino compound(s) chosen from polyamines, alkoxylated polyamines, alkyl monoamines, alkoxylated monoamines and mixtures thereof is from 1:10 to 10:1, and more preferably is from 1:5 to 5:1 and, even more preferably is from 1:2 to 2:1. Also, the composition remains clear when diluted with any ratio or amount of additional solvent.

Acid and amine numbers are generally determined by acid-base titration in the presence of a color indicator based on the European and American Pharmacopoeias and Standard ISO 660.

Lipophilic Compound

The at least one lipophilic compound may, for example, be chosen from oils, fatty esters, hydrocarbon oils, silicones different from alkoxylated silicone acids of the present invention, waxes, fatty acids and salts thereof, fatty alcohols, lipophilic vitamins and esters thereof, organic sunscreens, phospholipids, and mixtures thereof.

Non-limiting examples of oils include plant oils such as olive oil, avocado oil, coconut oil, safflower oil, almond oil, castor oil, jojoba oil, peanut oil, sesame oil, hazelnut oil, sunflower oil, apricot kernel oil, grapeseed oil, linseed oil and palm oil.

Non-limiting examples of hydrocarbon oils include mineral oil, petrolatum, and $C_{10}$-$C_{40}$ hydrocarbons which may be aliphatic (with a straight, branched or cyclic chain), aromatic, arylaliphatic such as paraffins, iso-paraffins, isododecanes, aromatic hydrocarbons, and mixtures thereof.

Non-limiting examples of silicones include phenyltrimethicone, dimethicone, cyclomethicone, dimethicone copolyol, laurylmethicone copolyol, cetyl dimethicone, dimethicone copolyol lactate, and polyorganosiloxanes such as polydimethylsiloxane.

Non-limiting examples of waxes include paraffin wax, beeswax, candelilla wax, carnauba wax, jasmine wax, jojoba wax and mimosa wax.

Suitable fatty acids include those containing from 8 to 30, preferably from 12 to 24 carbon atoms, and carboxylate salts of fatty acids. The sodium, potassium, ammonium, calcium and magnesium carboxylates of fatty acids listed are typical examples of the carboxylate salts of the fatty acids.

Non-limiting preferred examples of fatty alcohols include compounds of formula:

where R represents a hydrocarbon radical containing at least three carbon atoms, preferably from 8 to 30, more preferably from 12 to 24 carbon atoms, and which may be linear or branched, acyclic or cyclic, saturated or unsaturated, aliphatic or aromatic, substituted or unsubstituted. Typically, R is a linear or branched, acyclic alkyl or alkenyl group or an alkyl phenyl group.

Non-limiting preferred fatty esters include esters formed from fatty acids and $C_{1-10}$ alcohols and esters formed from the fatty alcohols as defined hereabobe and $C_{1-10}$ carboxylic acids.

According to a preferred embodiment, the at least one lipophilic compound is chosen from isopropyl palmitate, capric/caprylic triglyceride, isodecyl neopentanoate, polyisobutylene, phloretin, ellagic acid, vitamin D, vitamin E, vitamin E acetate, vitamin A, vitamin A palmitate, 2-oleamido-1,3-octadecanediol, octyl methoxycinnamate, octyl salicylate, 18-methyleicosanoic acid, and mixtures thereof.

The at least one lipophilic compound is present in the composition in a preferred amount of from 0.1 to 50% by weight, more preferably from 0.1 to 30% by weight, and even more preferably from 0.5 to 15% by weight, based on the total weight of the composition.

Solvent

The solvent is typically present in an amount from 10 to 95% by weight, preferably from 50 to 85% by weight, and more preferably from 60 to 80% by weight, based on the total weight of the composition. The solvent comprises water such as deionized water, alone or in combination with at least one $C_1$-$C_4$ alcohol. Alcohols include ethanol, propanol and butanol. Preferably, the alcohol is chosen from ethanol, isopropanol and mixtures thereof.

The solvent preferably comprises at least 20% by weight of water, more preferably at least 50% by weight, even more preferably at least 80% by weight, based on the total weight of the solvent.

Auxiliary Ingredients

The composition may optionally contain at least one auxiliary ingredient. The auxiliary ingredients may include in particular film forming agents, proteins, amino acids, cationic conditioners, cationic polymers, nonionic surfactants, anionic surfactants, amphoteric surfactants, zwitterionic surfactants, viscosity modifiers, antibacterial agents, sunscreens, preservatives, pH adjusting agents, bleaching agents, hair dyeing agents, perfumes, sequestering agents, anti-dandruff agents, alpha or beta hydroxy acids or alpha ketoacids, and mixtures thereof.

Non-limiting examples of film forming agents can be chosen from anionic compounds, non-ionic compounds, amphoteric compounds, zwitterionic compounds, proteins, viscosity modifiers, cationic polymers, polyamides, polyaminoamides, polyesters, silicone resins, polysaccharides, silicone fluids, polyacrylamides, starches, gums and mixtures thereof.

Non-limiting examples of proteins include collagen, deoxyribonuclease, iodized corn protein, milk protein, protease, serum protein, silk, sweet almond protein, wheat germ protein, wheat protein, alpha and beta helix of keratin proteins, hair proteins, such as intermediate filament proteins, high-sulfur proteins, ultrahigh-sulfur proteins, intermediate filament-associated proteins, high-tyrosine proteins, high-glycine tyrosine proteins, tricohyalin, and mixtures thereof.

Non-limiting examples of amino acids include amino acids derived from the hydrolysis of various proteins as well as the salts, esters, and acyl derivatives thereof. Non-limiting examples of such amino acid agents include amphoteric amino acids such as alkylamido alkylamines, i.e. stearyl acetyl glutamate, capryloyl silk amino acid, capryloyl collagen amino acids, capryloyl keratin amino acids, capryloyl pea amino acids, cocodimonium hydroxypropyl silk amino acids, corn gluten amino acids, cysteine, glutamic acid, glycine, hair keratin amino acids, amino acids such as asparatic acid, threonine, serine, glutamic acid, proline, glycine, alanine, cystine, valine, methionine, isoleucine, leucine, tyrosine, phenylalanine, cysteic acid, lysine, histidine, arginine, cysteine, tryptophan, citrulline, lysine, silk amino acids, wheat amino acids and mixtures thereof.

Non-limiting examples of cationic conditioners include quaternium-27, behenamidopropyl PG-dimonium chloride, hydroxyethyl tallowedimonium chloride, stearalkonium chloride and cetrimonium chloride.

Non-limiting examples of cationic polymers include hexadimethrine chloride, polyquaternium-4, polyquaternium-6, polyquaternium-7, polyquaternium-10, polyquaternium-11, polyquaternium-16, polyquaternium-22 and polyquaternium-32.

Non-limiting examples of nonionic surfactants includes alkoxylated derivatives of the following: fatty alcohols, alkyl phenols, fatty acids, fatty acid esters and fatty acid amides, wherein the alkyl chain is in the $C_{12-50}$ range, typically in the $C_{16-40}$ range, more typically in the $C_{24}$ to $C_{40}$ range, and having from 1 to 110 alkoxy groups. The alkoxy groups are selected from the group consisting of $C_2$-$C_6$ oxides and their mixtures, with ethylene oxide, propylene oxide, and their mixtures being the typical alkoxides. The alkyl chain may be linear, branched, saturated, or unsaturated. Of these alkoxylated non-ionic surfactants, the alkoxylated fatty alcohols are preferred, and the ethoxylated alcohols and propoxylated alcohols are more preferred. The alkoxylated alcohols may be used alone or in mixtures with those alkoxylated materials disclosed herein-above.

Representative preferred examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10), steareth-10 (a stearyl alcohol ethoxylate having an average degree of ethoxylation of 10), steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and mixtures of the precedings.

Commercially available corresponding nonionic surfactants are for example Brij® nonionic surfactants from Croda, Inc., Edison, N.J. Typically, Brij® is the condensation products of aliphatic alcohols with from 1 to 54 moles of ethylene oxide, the alkyl chain of the alcohol being typically a linear chain and having from 8 to 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. $C_8$-$C_{30}$ alcohols, with sugar or starch polymers. These compounds can be represented by the formula (S)n-O—R wherein S is a sugar moiety such as glucose, fructose, mannose, galactose, and the like; n is an integer of from 1 to 1000, and R is a $C_8$-$C_{30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a $C_8$-$C_{20}$ alkyl group, and n is an integer of from 1 to 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, typically glyceryl monoesters of $C_{16}$-$C_{22}$ saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of $C_{16}$-$C_{22}$ saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of $C_{16}$-$C_{22}$ fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel° 83 from Croda, Inc., Edison, N.J.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use as nonionic surfactants are alkoxylated derivatives of glyceryl esters, sorbitan esters, and alkyl polyglycosides, wherein the alkoxy groups is selected from the group consisting of $C_2$-$C_6$ oxides and their mixtures, with ethoxylated or propoxylated derivatives of these materials being typical. Nonlimiting examples of commercially available ethoxylated materials include ethoxylated sorbitan mono-, di- and/or tri-esters of $C_{12}$ to $C_{18}$ fatty acids with an average degree of ethoxylation of from 2 to 20, such as the products sold under the name TWEEN® by the company Uniqema).

Non-limiting examples of anionic surfactants include compounds in the classes known as alkyl sulfates, alkyl ether sulfates, alkyl sulfonates, alkyl ether sulfonates, sulfate esters of an alkylphenoxy polyoxyethylene ethanol, alpha-olefin sulfonates, beta alkyloxy alkene sulfonates, alkyl arylsulfonates, alkyl carbonates, alkyl ether carboxylates, fatty acids, succinamates, sulfosuccinates, sarcosinates, octoxynol or nonoxynol phosphates, taurates, fatty taurides, sulfated monoglycerides, fatty acid amino polyoxyethylene sulfates, isethionates and mixtures thereof. Specific examples of anionic surfactants include the ammonium, monoethanolamine, diethanolamine, triethanolamine, isopropylamine, sodium, potassium, lithium, or magnesium salts of lauryl sulfate, dodecylbenzene-sulfonate, lauryl sulfosuccinate, lauryl ether sulfate, lauryl ether carboxylate, lauryl sarcosinate, cocomethyl tauride, and sulfosuccinate half ester amide and mixtures thereof.

Non-limiting examples of amphoteric and zwitterionic surfactants include alkyl, alkyl dimethyl, alkylamido, alkyl amide, alkylamidopropyl, or alkyl dimethylammonium betaine; alky amidopropyl or alkyl sulfobetaine; alkyl, alkylampho, or alkylamphocarboxy glycinate; alkyl, or alkyl substituted imidazoline mono or dicarboxylate; sodium salts of alkyl mono- or dicarboxylates; alkyl beta amino acids; alkyl amidopropyl, or alkyl ether hydroxysultaine; alkyl amidopropyl dimethyl ammonia acetate; alkyl ampho mono- or diacetate; alkyl, or alkyl ampho, or alkyl imino dipropionate; alkyl amphopropionate; alkyl beta amino propionic acid; alkyl dipropionate; alkyl beta iminodipropionate; branched or n-alkyl dimethylamidopropionate; alkyl carboxylated propionate; alkyl, or methyl alkyl imidazoline; fluorinated alkyl amphoteric mixtures.

Specific examples include cocamidopropyl betaine, lauramidopropyl betaine, coco/oleamidopropyl betaine, coco betaine, oleyl betaine, cocamidopropyl hydroxysultaine, tallowamidopropyl hydroxysultaine and dihydroxyethyl tallow glycinate and mixtures thereof.

Non-limiting examples of viscosity modifiers include water swellable/soluble cationic polymers from quaternized polysaccharides such as trimethyl ammonium substituted epoxide of hydroxyethyl cellulose, diallyldimethyl ammonium salts of hydroxyethylcellulose, deacylated chitin or chitosan, dihydroxypropyl chitosan trimonium chloride, hydroxypropltrimethyl ammonium chloride guar, locust bean, or konjac mannan gum; quaternized synthetics such as acrylamide dimethyl diallyl ammonium chloride copolymers, acrylamide/dimethyl diallyl ammonium chloride/ acrylic acid terpolymer, quaternized poly (vinyl pyrrolidone/ dimethyl amino ethylmethacrylate), poly (vinylpyrrolidone/ methacrylamidopropyl trimethylammonium chloride), polyvinyl pyrrolidone/methylvinylimidazolinium chloride or methyl sulfate copolymer, chloroethylether/dimethylaminopropylamine/adipate or azelate terpolymer, vinylpyrrolidone/methacrylamidopropyl trimethylammonium chloride, acrylonitrile/acrylic acid/dimethylpropanediammonium acrylates sulfate terpolymer.

Further suitable viscosity modifiers include anionic or nonionic polysaccharide polymers such as gum tragacanth, sodium or propylene glycol alginate, kappa-, iota-, or lambda-carrageenan, guar or hydroxylpropyl guar gum, karaya gum, gum arabic, locust bean gum, konjac mannan gum, gellan, xanthan, succinoglycan or its acidic or enzymatic hydrolysates, sodium carboxymethyl cellulose, methycellulose, hydroxylethylcellulose, hydroxypropylmethylcellulose, and hydroxypropylcellulose; and/or hydrophobically modified anionic, cationic, or nonionic polymers such as, but not limited to, alkyl and/or substituted hydroxyethylcellulose, lauryl dimethyl ammonium substituted epoxide of hydroxyethylcellulose, propoxylated cellulosic, xanthan, succinoglycan, or polygalactomannoses, alkyl methacrylates/crosslinked acrylic acid copolymer and/or acrylonitrile/acrylates block copolymer.

Non-limiting examples of antibacterial agents include bacitracin, phenol, benzethonium chloride, erythromycin, neomycin, tetracycline, chlortetracycline and mixtures thereof.

Non-limiting examples of sunscreens include benzophenones, bornelone, butyl PABA, cinnamidopropyl trimethyl ammonium chloride, disodium distryrylbiphenyl disulfonate, PABA, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, ethylhexyl dimethyl PABA, red petrolatum, and mixtures thereof.

Non-limiting examples of preservatives include polyvinyl alcohol, phenoxyethanol, benzyl alcohol, methyl paraben, propyl paraben and mixtures thereof.

Non-limiting examples of pH adjusting agents include potassium acetate, sodium carbonate, sodium hydroxide, phosphoric acid, succinic acid, sodium citrate, citric acid, boric acid, lactic acid, sodium hydrogen carbonate and mixtures thereof.

Bleaching agents include, but are not limited to, hydrogen peroxide, perborate and persufate salts. EDTA and other aminocarboxylates may be used as sequestering agents. Anti-dandruff agents such as zinc pyrithione, salicylic acid, climbazole, ketoconazole, sulfur piroctone olamine, selenium sulfide and mixtures thereof may also be used as an auxiliary ingredient.

The alpha hydroxy acids may exist in the keto acid form, or the ester form. Examples of such alpha hydroxy acids include glycolic acid, malic acid, pyruvic acid, mandelic acid, lactic acid, methyllactic acid, and mixtures thereof.

Also beta hydroxy acids such as salicylic acid, and derivatives thereof may be included in the compositions of the present invention. In addition, mixtures of the above alpha and beta hydroxyl acids or alpha ketoacids can be advantageously included.

The compositions described above are useful as compositions for treating keratinous substrates. These compositions include hair care products such as shampoos and conditioners, products for treating skin such as skin cleansers and personal hygiene products and products for cleaning and treating lips and nails.

For example, when the keratinous substrate being treated is hair, the compositions of the invention may impart shine, conditioning, color retention in particular when the compositions are formulated into a rinse-off product. In this case, the method of the present invention will include a rinsing step usually performed with water, after a leave-on time of the composition of at least 30 seconds.

Similar properties, along with styling, may be provided when the composition is in the form of a leave-on product.

When the keratinous substrate is skin, the compositions may impart protection from the sun (sunscreens) or provide skin benefits by serving as a carrier vehicle for skin actives (anti-acne, anti-wrinkle, etc.).

The method of treatment to be provided will depend on the keratinous substrate being targeted and, consequently, the specific ingredients contained in the composition used to effectuate the treatment. One of ordinary skill in the art will easily be able to determine these variables. Regardless of the type of treatment and/or the type of keratinous substrate chosen, the method of treatment will be performed by a composition which is clear in appearance, regardless of the degree of dilution.

EXAMPLE

The following examples are for illustrative purposes only and are not intended to limit the scope of the claims.

Example 1

Various compositions (all of them qs to 100% with water), each containing a lipophilic compound, were prepared using the ingredients listed in Table 1 below, in which all quantities as expressed as percentages by weight with regard to the total weight of the composition.

These compositions were characterized as either clear or opaque using the McFarland scale. The McFarland scale is based on the McFarland Equivalence Turbidity Standard Test (Remel, 12076 Santa Fe Drive, Lenexa, Kans. 66215, USA). McFarland standards are used most commonly in microbiology as a reference to measure turbidity of bacterial suspensions in test tubes. The standards are generally prepared suspensions of either barium chloride or latex that range from a scale of 0.5 to 4. The higher the number, the more turbid the suspension. The latex suspension standard was used in this study.

Each composition in this study was placed into a clear glass test tube and was visually compared to the McFarland standards against a white card with contrasting black lines. A composition that did not exhibit phase separation, but visually appeared to possess a McFarland turbidity standard value of greater than 0.5 (>0.5) on the McFarland scale was deemed to be opaque. Conversely, a composition that did not exhibit phase separation, but visually appeared to possess a McFarland turbidity standard value equal to, or less than 0.5 (≤0.5) on the McFarland scale was deemed to be clear.

TABLE 1

| | Alkoxylated silicone acid | Alkoxylated polyamine | Lipophilic compound | Properties |
|---|---|---|---|---|
| 1a. | dimethicone PEG-8 phosphate, 23.25% | Jeffamine D-230, 1.0% | isodecyl neopentanoate, 1.0% | ≤0.5 (clear + homogeneous) |
| 1b. | dimethicone PEG-8 phosphate, 23.25% | — | isodecyl neopentanoate, 1.0% | >0.5 (opaque) |

TABLE 1-continued

| | Alkoxylated silicone acid | Alkoxylated polyamine | Lipophilic compound | Properties |
|---|---|---|---|---|
| 1c. | — | Jeffamine D-230, 1.0% | isodecyl neopentanoate, 1.0% | Phases separated |
| 2a. | dimethicone PEG-8 phosphate, 17.647% | Jeffamine T-403, 1.0% | isodecyl neopentanoate 1.0% | ≤0.5 (clear + homogeneous) |
| 2b. | dimethicone PEG-8 phosphate, 17.647% | — | isodecyl neopentanoate, 1.0% | >0.5 (opaque) |
| 2c. | — | Jeffamine T-403, 1.0% | isodecyl neopentanoate, 1.0% | Phases separated |

The dimethicone PEG-8 phosphate used in the compositions of this example 1 as well as in all examples hereafter is the product sold under the name Silsense PE-100L Silicone by the company Lubrizol.

Jeffamine D-230 belongs to the Jeffamine® D series by Hunstman of amine terminated PPGs (polypropylene glycols) and Jeffamine T-403 belongs to the Jeffamine® Triamines (T series) which are triamines made by reacting PO with a triol initiator followed by aminating the terminal hydroxyl groups.

The results above show that the compositions having either the alkoxylated polyamine or the alkoxylated silicone acid exhibited phases separation or appeared cloudy (>0.5 rating on the McFarland scale). In contrast, the compositions having both the alkoxylated polyamine and the alkoxylated silicone acid did not exhibit phases separation and were clear (≥0.5 rating on the McFarland scale).

Example 2

Various compositions (all of them qs to 100% with water), each containing a lipophilic compound, were prepared using the ingredients listed in Table 2 below, in which all quantities as expressed as percentages by weight with regard to the total weight of the composition.

These compositions were characterized as either clear or opaque using the McFarland scale, using the same procedure as in example 1 above.

TABLE 2

| | Alkoxylated silicone acid | Alkyl monoamine | Lipophilic compound | Properties |
|---|---|---|---|---|
| 1a. | dimethicone PEG-8 phosphate, 8.0% | oleamidopropyl dimethylamine, 3.0% | isodecyl neopentanoate, 1.0% | ≤0.5 (clear + homogeneous) |
| 1b. | dimethicone PEG-8 phosphate, 8.0% | — | isodecyl neopentanoate, 1.0% | >0.5 (opaque) |
| 1c. | — | oleamidopropyl dimethylamine, 3.0% | isodecyl neopentanoate, 1.0% | Phases separated |

The results above show that the compositions having either the alkyl monoamine or the alkoxylated silicone acid exhibited phases separation or appeared cloudy (>0.5 rating on the McFarland scale). In contrast, the composition having both the alkyl monoamine and the alkoxylated silicone acid did not exhibit phases separation and was clear (≥0.5 rating on the McFarland scale).

Example 3

Various compositions (all of them qs to 100% with water), each containing a lipophilic compound, were prepared using the ingredients listed in Table 3 below, in which all quantities as expressed as percentages by weight with regard to the total weight of the composition.

These compositions were characterized as either clear or opaque using the McFarland scale, using the same procedure as in example 1 above.

TABLE 3

| | Alkoxylated silicone acid | Polyamine | Lipophilic compound | Properties |
|---|---|---|---|---|
| 1a. | dimethicone PEG-8 phosphate, 23.24% | PEI-35, 0.5% | isodecyl neopentanoate, 1.0% | ≤0.5 (clear + homogeneous) |
| 1b. | dimethicone PEG-8 phosphate, 23.24% | — | isodecyl neopentanoate, 1.0% | >0.5 (opaque) |
| 1c. | — | PEI-35, 0.5% | isodecyl neopentanoate, 1.0% | Phases separated |

The results above show that the compositions having either the polyamine or the alkoxylated silicone acid exhibited phases separation or appeared cloudy (>0.5 rating on the McFarland scale). In contrast, the composition having both the polyamine (PEI-35 which means polyethyleneimine 35) and the alkoxylated silicone acid did not exhibit phase separations and was clear (≥0.5 rating on the McFarland scale).

Example 4

Various compositions (all of them qs to 100% with water), each containing a lipophilic compound, were prepared using the ingredients listed in Table 4 below, in which all quantities as expressed as percentages by weight with regard to the total weight of the composition.

These compositions were characterized as either clear or opaque using the McFarland scale, using the same procedure as in example 1 above.

TABLE 4

| | Alkoxylated silicone acid | Alcoxylated monoamine | Lipophilic compound | Properties |
|---|---|---|---|---|
| 1a. | dimethicone PEG-8 phosphate, 7.28% | PEG-2 oleamine, 2.0% | isodecyl neopentanoate, 1.0% | ≤0.5 (clear + homogeneous) |
| 1b. | dimethicone PEG-8 phosphate, 7.28% | — | isodecyl neopentanoate, 1.0% | >0.5 (opaque) |
| 1c. | — | PEG-2 oleamine, 2.0% | isodecyl neopentanoate, 1.0% | Phases separated |

The results above show that the compositions having either the alkoxylated monoamine or the alkoxylated silicone acid exhibited phases separation or appeared cloudy (>0.5 rating on the McFarland scale). In contrast, the composition having both the alkoxylated monoamine and the alkoxylated silicone acid did not exhibit phase separations and was clear (≥0.5 rating on the McFarland scale).

Examples 5 to 9 hereunder illustrate the conditioning efficiency of the compositions of the present invention.

Example 5

Bleached hair swatches were dyed red with a commercial coloring product (Redken Hi Fusion™ R, 20 Vol., 30 min. at room temperature). The initial color values of the dyed hair was measured using the LAB system, in which the parameter L denotes the intensity, the parameter A denotes the color on the green/red color axis and B denotes the color on the blue/yellow color axis.

The dyed swatches were then treated with the following compositions (all quantities being expressed as percentages by weight):
Treatment 1: Composition made of 7.28% dimethicone PEG-8 phosphate (Silsense PE-100L Silicone); 2% PEG-2 oleamine; 1% isodecyl neopentanoate; 89.72% water (clear composition)
Treatment 2: Composition made of 7.28% dimethicone PEG-8 phosphate (Silsense PE-100L Silicone); 1% isodecyl neopentanoate; 91.72% water (opaque composition)
Treatment 3: Composition made of 2% PEG-2 oleamine; 1% isodecyl neopentanoate; 97% water (phases separated)
Treatment 4: Composition made of 1% isodecyl neopentanoate; 99% water (phases separated)
Treatment 5: Composition made of 7.28% dimethicone PEG-8 phosphate (Silsense PE-100L Silicone); 2% PEG-2 oleamine; 90.72% water (clear composition).

The compositions were stirred vigorously before the treatment, then applied on the hair using 0.4 g of composition/g of hair as leave-on treatments, using 6 hair swatches per treatment.

The treated hair swatches were then shampooed with an aqueous solution containing 10% by weight of sodium laurylethersulfate 20E, having a pH of 6, using 0.4 g of shampoo/g of hair, for 15 seconds and then rinsed with water for 10 seconds. The treatment-shampoo cycle was repeated for a total of 5 times.

The final LAB value of the shampooed hair swatches was determined and the change in the total color (Delta E) was calculated, according to the following formula:

$$\text{Delta } E = [(L_0-L_1)^2 + (A_0-A_1)^2 (B_0-B_1)^2]^{1/2}$$

wherein $L_0$, $A_0$, and $B_0$ are relating to the dyed hair before treatment and shampoo of the hair, and $L_1$, $A_1$ and $B_1$ are relating to the hair after treatment and shampoo of the hair.

The lower the value of Delta E, the less the color was altered by the treatment-shampoo cycles.

The results are shown below:

| Treatment | Delta E |
|---|---|
| 1 | 4.82 |
| 2 | 11.95 |
| 3 | 13.12 |
| 4 | 16.89 |
| 5 | 8.81 |

The data indicate that hair treated with Treatment 1 has the lowest Delta E which is significantly lower than the Delta E obtained with all other treatments. Therefore, the presently claimed composition imparts a color protection to hair, which is significantly better than any other compositions lacking one or more of its components.

Example 6

Bleached hair swatches were dyed red with a commercial coloring product (Redken Hi Fusion™ R, 20 Vol., 30 min. at room temperature). The initial LAB value of the hair was determined as indicated in example 5.

The dyed swatches were then treated with the following compositions (all quantities being expressed as percentages by weight):
Test Treatment Composition made of 23.24% dimethicone PEG-8 phosphate (Silsense PE-100L Silicone), 1% Jeffamine D-230, 1% isodecyl neopentanoate, water Q.S. to 100% (clear composition)
Control Treatment: Composition made of 23.24% dimethicone PEG-8 phosphate (Silsense PE-100L Silicone), 1% isodecyl neopentanoate, water Q.S. to 100% (opaque composition)

The compositions were applied on the hair using 0.4 g of composition/g of hair as leave-on treatments, using 6 hair swatches per treatment.

The treated hair swatches were then shampooed with an aqueous solution containing 10% by weight of sodium laurylethersulfate 20E, having a pH of 6, using 0.4 g of shampoo/g of hair, for 15 seconds and then rinsed with water for 10 seconds. The treatment-shampoo cycle was repeated for a total of 8 times.

The final LAB value of the shampooed hair swatches was taken and the change in the total color (Delta E) was calculated as indicated in example 5.

The results are shown below:

| Treatment | Delta E |
|---|---|
| Test treatment | 23.59 |
| Control treatment | 26.49 |

The data indicate that hair treated with the test treatment has the lowest Delta E which is significantly different from control treatment. Therefore, the presently claimed composition imparts a color protection to hair, significantly better than the comparative composition.

Example 7

6 natural level hair swatches were shampooed twice using an aqueous solution containing 15% by weight of sodium laurylethersulfate 20E, having a pH of 6, for 30 seconds and then rinsed with water for 30 seconds.

The initial wet comb measurements of such swatches were taken using an Instron device. The swatches were then treated with the following compositions (all quantities being expressed as percentages by weight):
Test Treatment Composition made of 23.24% dimethicone PEG-8 phosphate (Silsense PE-100L Silicone), 1% Jeffamine D-230, 1% isodecyl neopentanoate, water Q.S. to 100% (clear composition)
Control Treatment: Composition made of 23.24% dimethicone PEG-8 phosphate (Silsense PE-100L Silicone), 1% isodecyl neopentanoate, water Q.S. to 100% (opaque composition)

The compositions were applied on the hair using 0.5 g of composition/g of hair as leave-on treatments for 5 minutes, using 3 hair swatches per treatment. The compositions were then rinsed off under water for 15 seconds.

Final wet comb measurements were taken and the percentage of change in energy to comb was calculated: the percentage of change in energy to comb for test treatment was −57.37 and for control treatment was 15.05.

These results indicate that hair treated with test treatment has the lower percentage change in combing energy, which is significantly lower than the value obtained for the control treatment. Therefore, the presently claimed composition imparts a significantly better wet combing to the hair.

Example 8

Bleached hair swatches were dyed red with a commercial coloring product (Redken Hi Fusion™ R, 20 Vol., 30 min. at room temperature). The initial LAB value of the hair was taken as indicated in example 5.

The dyed swatches were then treated with the following compositions (all quantities being expressed as percentages by weight):
Test Treatment Composition made of 8% dimethicone PEG-8 phosphate (Silsense PE-100L Silicone), 3% oleamidopropyl dimethylamine, 1% isodecyl neopentanoate, water Q.S. to 100% (clear composition)
Control Treatment: Composition made of 8% dimethicone PEG-8 phosphate (Silsense PE-100L Silicone), 1% isodecyl neopentanoate, water Q.S. to 100% (opaque composition)
No Treatment: untreated. (shampoo-only)

The compositions were stirred vigorously before the treatment, then applied on the hair using 0.4 g of composition/g of hair as leave-on treatments, using 6 hair swatches per treatment.

The treated hair swatches were then shampooed with an aqueous solution containing 10% by weight of sodium laurylethersulfate 20E, having a pH of 6, using 0.4 g of shampoo/g of hair, for 15 seconds and then rinsed with water for 10 seconds. The treatment-shampoo cycle was repeated for a total of 5 times.

The final LAB value of the shampooed hair swatches was taken and the change in the total color (Delta E) was calculated as indicated in example 5.

The results are shown below:

| Treatment | Delta E |
| --- | --- |
| Test treatment | 8.93 |
| Control treatment | 10.86 |
| No treatment | 15.00 |

The data indicate that hair treated with the test treatment has the lowest Delta E which is significantly lower than the Delta E obtained with control treatment and no treatment (shampoo-only). Therefore, the presently claimed composition imparts a color protection to hair, significantly better than the comparative composition and than no treatment.

Example 9

Bleached hair swatches were dyed red with a commercial coloring product (Redken Hi Fusion R, 20 Vol., 30 min. at room temperature). The initial LAB value of the hair was measured as indicated in example 5

The dyed swatches were then treated with the following compositions (all quantities being expressed as percentages by weight):
Test Treatment Composition made of 23.24% dimethicone PEG-8 phosphate (Silsense PE-100L Silicone), 0.5% polyethyleneimine (PEI-35), 1% isodecyl neopentanoate, water Q.S. to 100% (clear composition)
Control Treatment: Composition made of 23.24% dimethicone PEG-8 phosphate (Silsense PE-100L Silicone), 1% isodecyl neopentanoate, water Q.S. to 100% (opaque composition)
No Treatment: untreated. (shampoo-only)

The compositions were applied on the hair using 0.4 g of composition/g of hair as leave-on treatments, using 6 hair swatches per treatment.

The treated hair swatches were then shampooed with an aqueous solution containing 10% by weight of sodium laurylethersulfate 20E, having a pH of 6, using 0.4 g of shampoo/g of hair, for 15 seconds and then rinsed with water for 10 seconds. The treatment-shampoo cycle was repeated for a total of 5 times.

The final LAB value of the shampooed hair swatches was taken and the change in the total color (Delta E) was calculated as indicated in example 5.

The results are shown below:

| Treatment | Delta E |
| --- | --- |
| Test treatment | 7.01 |
| Control treatment | 8.89 |
| No treatment | 15.00 |

The data indicate that hair treated with the test treatment has the lowest Delta E which is significantly lower than the values obtained with control treatment and no treatment (shampoo-only). Therefore, the presently claimed composition imparts a color protection to hair, significantly better than the comparative composition and than no treatment.

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

What is claimed is:
1. A composition comprising:
(a) at least one alkoxylated silicone acid;
(b) at least one amino compound chosen from polyamines, alkoxylated polyamines, alkyl monoamines, alkoxylated monoamines and mixtures thereof;
(c) at least one lipophilic compound; and
(d) at least one solvent comprising water; and
wherein the composition does not contain a nonionic surfactant.

2. The composition of claim 1, wherein the at least one alkoxylated silicone acid is chosen from alkoxylated silicone carboxylates, alkoxylated silicone phosphates, alkoxylated silicone sulfates, alkoxylated silicone sulfosuccinates, alkoxylated silicone sulfonates and mixtures thereof, in which the alkoxy groups are preferably chosen from ethylene oxide groups, propylene oxide groups and mixtures thereof.

3. The composition of claim 1, wherein the at least one alkoxylated silicone acid is chosen from dimethicone PEG-8 phosphate, dimethicone PEG-7 phosphate and mixtures thereof.

4. The composition of claim 1, wherein the at least one alkoxylated silicone acid is present in an amount of from 1 to 50% by weight based on the total weight of the composition.

5. The composition claim 1, wherein the at least one alkoxylated silicone acid is present in an amount of from 2 to 40% by weight, based on the total weight of the composition.

6. The composition of claim 1, wherein the at least one alkoxylated silicone acid is present in an amount of from 5 to 30% by weight, based on the total weight of the composition.

7. The composition of claim 1, comprising at least one alkoxylated polyamine corresponding to:

those of formula (IA):

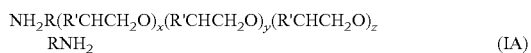

$$NH_2R(R'CHCH_2O)_x(R'CHCH_2O)_y(R'CHCH_2O)_z RNH_2 \quad (IA)$$

wherein R represents a —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted;

x, y, and z independently of one another, represent numbers of from 0 to 100;

R' represents hydrogen, or an alkyl group, preferably a methyl group; and the sum of x+y+z is at least 1;

those of formula (IIA):

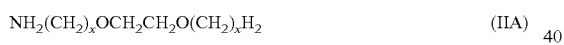

$$NH_2(CH_2)_xOCH_2CH_2O(CH_2)_xH_2 \quad (IIA)$$

wherein x is 2 or 3;

those of formula (IIIA):

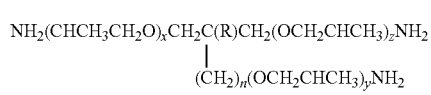

$$NH_2(CHCH_3CH_2O)_xCH_2C(R)CH_2(OCH_2CHCH_3)_zNH_2$$
$$|$$
$$(CH_2)_n(OCH_2CHCH_3)_yNH_2 \quad (IIIA)$$

wherein R is hydrogen or —C$_2$H$_5$,
n is 0 or 1, and
x, y, and z independently of one another, represent numbers of from 1 to 100 and the sum of x+y+z is at least 1;

those of formulas (IVA) and (VA):

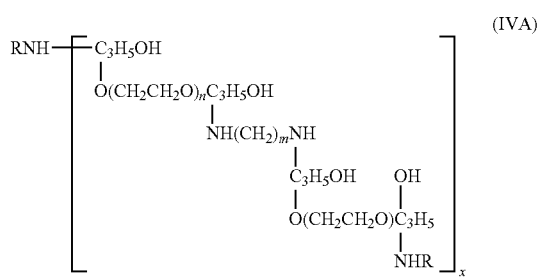

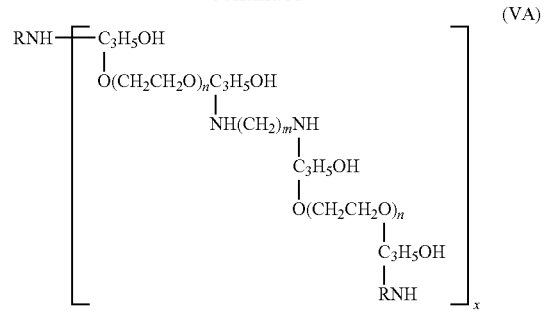

wherein
R in formula (IVA) represents the alkyl group derived from tallow and R in formula (VA) represents the alkyl group derived from coconut oil;
n in both formulas (IVA) and (VA) has a total value ranging from 10 to 20;
m in both formulas (IVA) and (VA) has a value ranging from 2 to 6; and
x in both formulas (IVA) and (VA) has a value ranging from 2 to 4.

8. The composition of claim 1, wherein the at least one alkoxylated polyamine is present in an amount ranging from 0.1 to 50% by weight, based on the total weight of the composition.

9. The composition of claim 1, wherein the at least one alkoxylated polyamine is present in an amount ranging from 0.5 to 15% by weight, based on the total weight of the composition.

10. The composition of claim 1, wherein the at least one alkoxylated polyamine is present in an amount ranging from 0.5 to 10% by weight, based on the total weight of the composition.

11. The composition of claim 1, comprising at least one alkyl monoamine chosen from:

aliphatic amine compounds corresponding to formula (IB) and their salts:

$$RN(R')_2 \quad (IB)$$

wherein
R is a hydrocarbon radical containing at least 6 carbon atoms;
R' is H or a hydrocarbon radical containing less than 6 carbon atoms;

amidoamine compounds corresponding to formula (IIB) and their salts:

$$RCONHR'N(R'')_2 \quad (IIB)$$

wherein:
R is a hydrocarbon radical containing at least 6 carbon atoms;
R' is a divalent hydrocarbon radical containing less than 6 carbon atoms; and
R" is H or a hydrocarbon radical containing less than 6 carbon atoms.

12. The composition of claim 1, wherein the at least one alkyl monoamine is present in an amount ranging from 0.1 to 50% by weight, based on the total weight of the composition.

13. The composition of claim 1, wherein the at least one alkyl monoamine is present in an amount ranging from 0.5 to 30% by weight, based on the total weight of the composition.

14. The composition of claim 1, wherein the at least one alkyl monoamine is present in an amount ranging from 1 to 20% by weight, based on the total weight of the composition.

15. The composition of claim 1, comprising at least one polyamine chosen from polyethyleneimines, polyvinylamines, aminated polysaccharides, amine substituted polyalkylene glycols, amine substituted polyacrylate crosspolymers, amine substituted polyacrylates, amine substituted polymethacrylates, proteins, protein derivatives, amine substituted polyesters, polyamino acids, polyalkylamines, diethylene triamine, triethylenetetramine, spermidine, spermine and mixtures thereof.

16. The composition of claim 1, wherein the at least one polyamine is a polyethyleneimine of formula (IC):

(CH$_2$CH$_2$NH)$n$  (IC)

wherein n is an integer ranging from 5 to 5000.

17. The composition of claim 1, wherein the at least one polyamine is present in an amount ranging from 0.1 to 50% by weight, based on the total weight of the composition.

18. The composition of claim 1, wherein the at least one polyamine is present in an amount ranging from 0.25 to 30% by weight, based on the total weight of the composition.

19. The composition of claim 1, wherein the at least one polyamine is present in an amount ranging from 0.5 to 15% by weight, based on the total weight of the composition.

20. The composition of claim 1, comprising at least one alkoxylated monoamine chosen from:
compounds corresponding to the formula (ID):

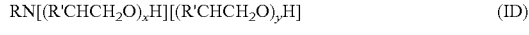

RN[(R'CHCH$_2$O)$_x$H][(R'CHCH$_2$O)$_y$H]  (ID)

wherein is a hydrocarbon radical containing at least 6 carbon atoms;
x and y, independently of one another, represent numbers of from 0 to 100 provided that the sum of x+y is >0;
the groups R', which may be identical or different, represent hydrogen, or an alkyl group;
compounds corresponding to formula (IID):

RNR"[(R'CHCH$_2$O)$_x$H]  (IID)

wherein is a hydrocarbon radical containing at least 6 carbon atoms;
x represents a number of from 1 to 100;
R' represents hydrogen, or an alkyl group; and
R" is a hydrogen or a hydrocarbon radical;
compounds corresponding to formula (IIID):

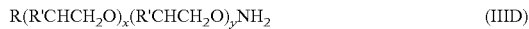

R(R'CHCH$_2$O)$_x$(R'CHCH$_2$O)$_y$NH$_2$  (IIID)

wherein is a hydrocarbon radical containing at least 6 carbon atoms;
x and y, independently of one another, represent numbers of from 0 to 100 with the proviso that the sum of x+y is >0;
the groups R', which may be identical or different, represent hydrogen, or an alkyl group.

21. The composition of claim 1, wherein the at least one alkoxylated monoamine is present in an amount ranging from 0.1 to 50% by weight, based on the total weight of the composition.

22. The composition of claim 1, wherein the at least one alkoxylated monoamine is present in an amount ranging from 0.5 to 30% by weight, based on the total weight of the composition.

23. The composition of claim 1, wherein the at least one alkoxylated monoamine is present in an amount ranging from 1 to 20% by weight, based on the total weight of the composition.

24. The composition of claim 1, wherein the ratio of the acid number of the at least one alkoxylated silicone acid to the total amine number of amino compound(s) chosen from polyamines, alkoxylated polyamines, alkyl monoamines, alkoxylated monoamines and mixtures thereof, is from 1:10 to 10:1.

25. The composition of claim 1, wherein the ratio of the acid number of the at least one alkoxylated silicone acid to the total amine number of amino compound(s) chosen from polyamines, alkoxylated polyamines, alkyl monoamines, alkoxylated monoamines and mixtures thereof, is from 1:5 to 5:1.

26. The composition of claim 1, wherein the ratio of the acid number of the at least one alkoxylated silicone acid to the total amine number of amino compound(s) chosen from polyamines, alkoxylated polyamines, alkyl monoamines, alkoxylated monoamines and mixtures thereof, is from 1:2 to 2:1.

27. The composition of claim 1, wherein the at least one lipophilic compound is chosen from oils, fatty esters, hydrocarbon oils, silicones different from said alkoxylated silicone acids, waxes, fatty acids and salts thereof, fatty alcohols, lipophilic vitamins and esters thereof, organic sunscreens, phospholipids, and mixtures thereof.

28. The composition of claim 1, wherein the at least one lipophilic compound is present in an amount of from 0.1 to 50% by weight, based on the total weight of the composition.

29. The composition of claim 1, wherein the at least one lipophilic compound is present in an amount of from 0.1 to 30% by weight, based on the total weight of the composition.

30. The composition of claim 1, wherein the at least one lipophilic compound is present in an amount of from 0.5 to 15% by weight, based on the total weight of the composition.

31. The composition of claim 1, wherein the solvent is present in an amount from 10 to 95% by weight, based on the total weight of the composition.

32. The composition of claim 1, wherein the solvent is present in an amount from 50 to 85% by weight, based on the total weight of the composition.

33. The composition of claim 1, wherein the solvent is present in an amount from 60 to 80% by weight, based on the total weight of the composition.

34. The composition of claim 1, wherein the solvent comprises water, alone or in combination with at least one C$_1$-C$_4$ alcohol.

35. The composition claim 1, wherein the solvent comprises at least 20% by weight of water.

36. The composition claim 1, wherein the solvent comprises at least 50% by weight of water.

37. The composition claim 1, wherein the solvent comprises at least 80% by weight of water.

38. A method of making a clear composition involving the steps of:
(a) providing at least one alkoxylated silicone acid;
(b) providing at least one amino compound chosen from polyamines, alkoxylated polyamines, alkyl monoamines, alkoxylated monoamines and mixtures thereof;
(c) providing at least one lipophilic compound;
(d) providing at least one solvent comprising water; and
(e) mixing the compounds as defined in steps (a) to (d) to form a composition that is clear in appearance; and
wherein the composition does not contain a nonionic surfactant.

39. A method of cosmetic treatment of a keratinous substrate involving the step of applying onto said keratinous substrate a composition comprising:
(a) at least one alkoxylated silicone acid;
(b) at least one amino compound chosen from polyamines, alkoxylated polyamines, alkyl monoamines, alkoxylated monoamines and mixtures thereof;
(c) at least one lipophilic compound; and
(d) at least one solvent comprising water; and wherein the composition does not contain a nonionic surfactant.

40. The method of claim 39, wherein the at least one alkoxylated silicone acid is chosen from alkoxylated silicone carboxylates, alkoxylated silicone phosphates, alkoxylated silicone sulfates, alkoxylated silicone sulfosuccinates, alkoxylated silicone sulfonates and mixtures thereof, in which the alkoxy groups are preferably chosen from ethylene oxide groups, propylene oxide groups and mixtures thereof.

41. The method of claim 39, wherein the at least one alkoxylated silicone acid is chosen from dimethicone PEG-8 phosphate, dimethicone PEG-7 phosphate and mixtures thereof.

42. The method of claim 39, wherein the at least one alkoxylated silicone acid is present in an amount of from 1 to 50% by weight, based on the total weight of the composition.

43. The method of claim 39, wherein the at least one amino compound chosen from polyamines, alkoxylated polyamines, alkyl monoamines, alkoxylated monoamines and mixtures thereof is present in an amount ranging from 0.1 to 50% by weight, based on the total weight of the composition.

44. The method of claim 39, wherein the ratio of the acid number of the at least one alkoxylated silicone acid to the total amine number of amino compound(s) chosen from polyamines, alkoxylated polyamines, alkyl monoamines, alkoxylated monoamines and mixtures thereof, is from 1:10 to 10:1.

45. The method of claim 39, wherein the at least one lipophilic compound is chosen from oils, fatty esters, hydrocarbon oils, silicones different from said alkoxylated silicone acids, waxes, fatty acids and salts thereof, fatty alcohols, lipophilic vitamins and esters thereof, organic sunscreens, phospholipids, and mixtures thereof.

46. The method of claim 39, wherein the solvent is present in an amount from 10 to 95% by weight, based on the total weight of the composition.

* * * * *